Figure 5:
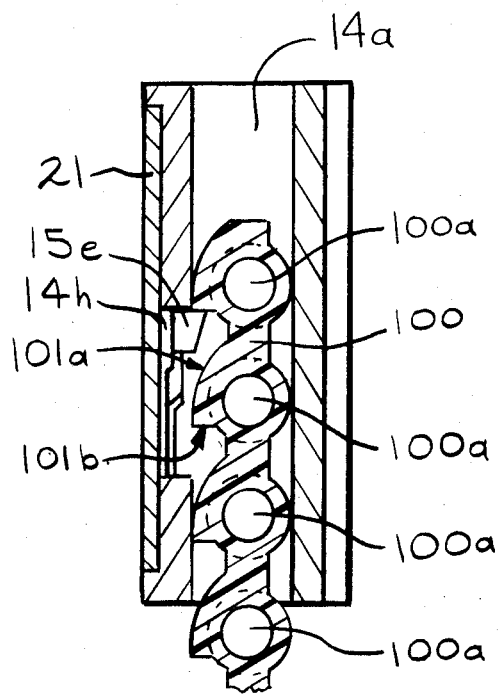

United States Patent [19]

Prindle et al.

[11] Patent Number: 4,687,465
[45] Date of Patent: Aug. 18, 1987

[54] AUTOMATIC CLIP OR PELLET CARRIER FED PELLET IMPLANTER APPARATUS

[75] Inventors: Gordon E. Prindle, Schaumburg; Thomas J. Kelm, Forest Park, both of Ill.

[73] Assignee: Ideal Instruments, Inc., Chicago, Ill.

[21] Appl. No.: 855,908

[22] Filed: Apr. 25, 1986

[51] Int. Cl.⁴ .............................................. A61M 5/00
[52] U.S. Cl. ...................................... 604/61; 604/62; 221/197; 124/45
[58] Field of Search ............................ 604/57, 59–64; 221/197, 198, 279; 124/45, 51

[56] References Cited

U.S. PATENT DOCUMENTS

| | | | |
|---|---|---|---|
| 3,669,104 | 6/1972 | Wyatt et al. ........................... | 604/61 |
| 4,004,565 | 1/1977 | Fischer et al. . | |
| 4,077,406 | 3/1978 | Sandhage et al. ................ | 604/62 X |
| 4,403,610 | 9/1983 | Lodge et al. . | |
| 4,447,223 | 5/1984 | Kaye et al. . | |
| 4,531,938 | 7/1985 | Kaye et al. . | |

FOREIGN PATENT DOCUMENTS 1583816  2/1981  United Kingdom ................ 604/62

Primary Examiner—Stephen C. Pellegrino
Attorney, Agent, or Firm—Ian C. McLeod

[57] ABSTRACT

An automatic clip or carrier 100 fed pellet implanting gun apparatus 10 is described. The gun uses a pivotable lever 15 with a projection 15e on arm 15b which engages an arcuate surface 101a of a cam 101 on the carrier and snaps into place adjacent a drive surface 101b of the cam when the trigger 36 is depressed and then the projection engages the drive surface to move a next adjacent a new chamber 100a into line with a barrel 13a of needle 13 and opening 14k in a head means so that rod 31 can again insert a pellet. The gun apparatus is particularly adapted to implant pellets in animals, particularly as medicament pellets.

14 Claims, 7 Drawing Figures

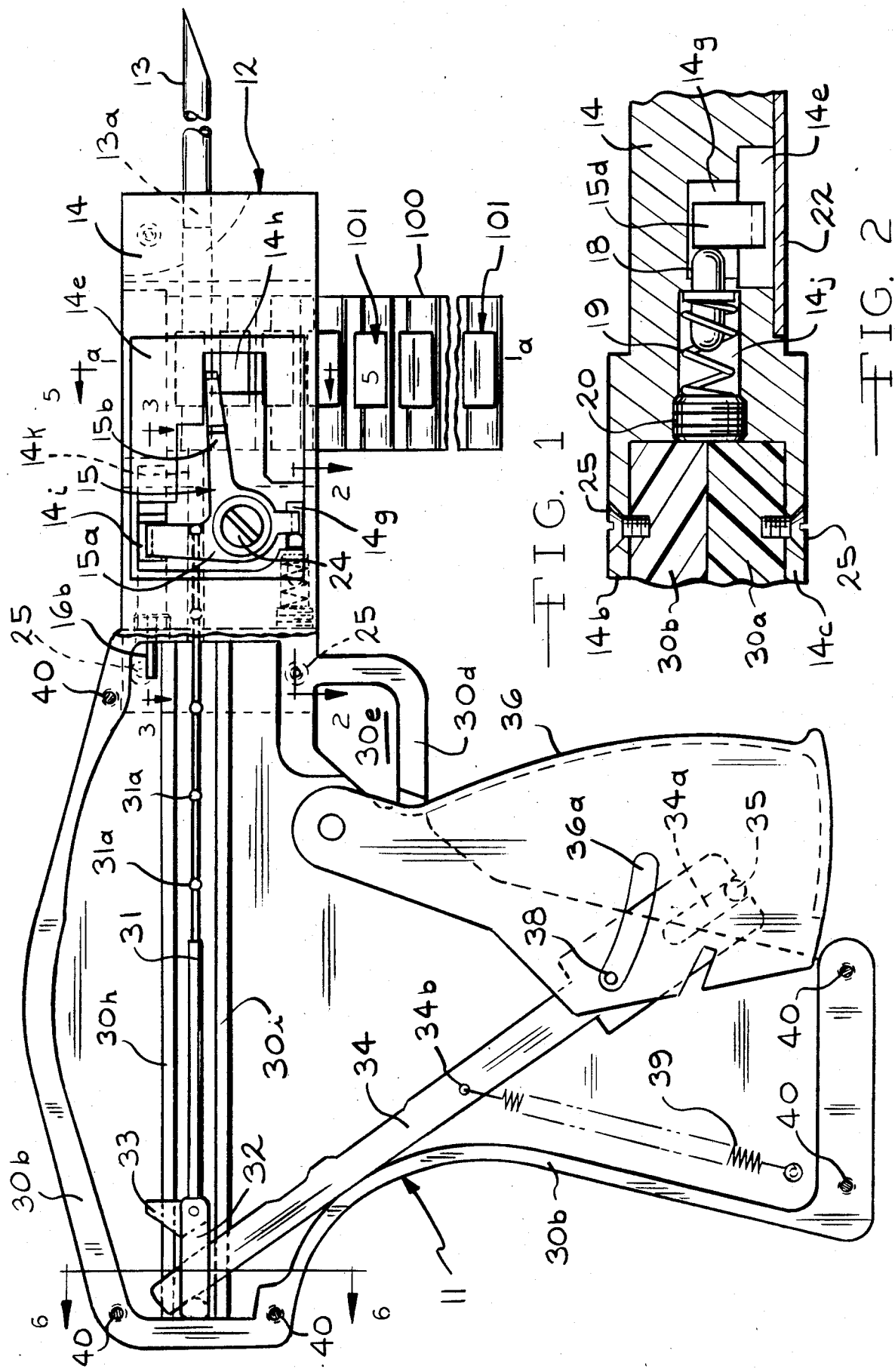

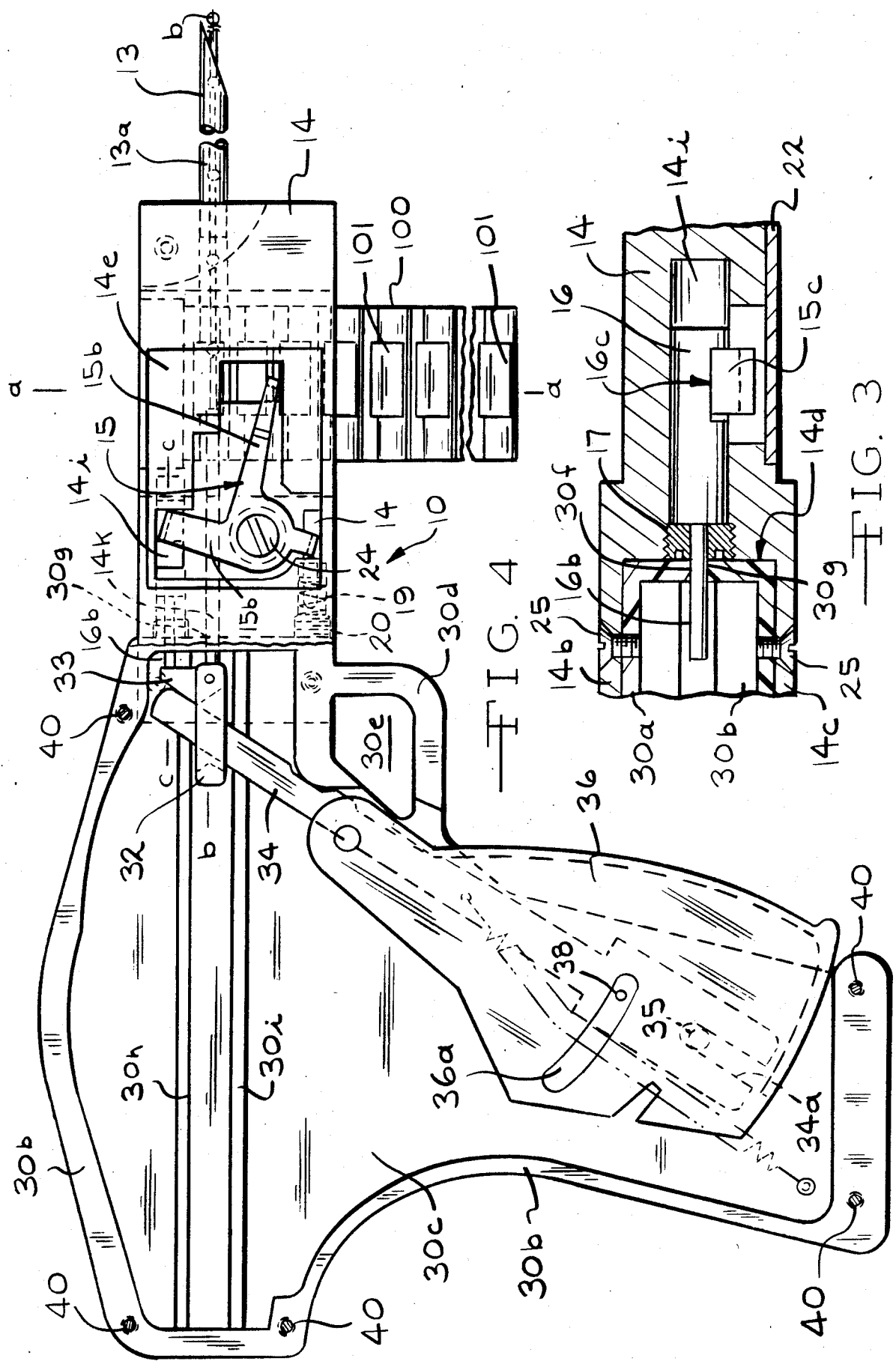

AUTOMATIC CLIP OR PELLET CARRIER FED PELLET IMPLANTER APPARATUS

BACKGROUND (1) Field of the Invention

The present invention relates to an automatic clip or pellet carrier fed pellet implanting apparatus for animals and the like. In particular the present invention relates to an automatic gun apparatus for implanting pellets which uses a trigger actuated lever which rotates to engage a cam on the outside of the carrier to advance the carrier. In particular the present invention relates to a lever which rotates over an arcuate surface of a cam and snaps into place adjacent a drive surface of the cam adjacent to the arcuate surface as the trigger is pulled and then the lever advances the carrier by engaging the drive surface when the trigger is released.

(2) Prior Art

The prior art has described hand held pellet implanting gun apparatus. The closest prior art is believed to be U.S. Pat. Nos. 4,077,406 to Sandhage et al; 4,403,610 to Lodge et al; and 4,447,223 to Kaye et al. Sandhage et al describe a non-automatic clip fed gun apparatus wherein the clip or pellet carrier is manually advanced in the gun. A spring detent 42 holds the clip and locates openings containing the pellets adjacent the barrel of a needle for implanting by movement of a trigger controlled rod 27. Lodge et al describe an automatic clip or carrier fed gun apparatus. In this apparatus, the clip is advanced by rods 24 on both sides of a carrier or magazine 12 which engage the underside of projections 25 on both sides of the magazine 12. A ball 32 detent engages a recess in the magazine 12 to hold it in place to prevent movement of the clip in the wrong direction. The construction of the gun and the magazine 12 with projections 24 requires considerable precision in order for the gun apparatus to function. Kaye et al describes a similar carrier advancing mechanism to Lodge et al. A cam 122 serves to move the clip or carrier for the pellets. The Kaye et al device has a retractable needle and would be relatively expensive to construct because of the precision required for the cam and the carrier. U.S. Pat. Nos. 4,004,565 to Fischer and 4,531,938 to Kaye et al describe cartridge type apparatus which are more remote from the present invention.

OBJECTS

It is therefore an object of the present invention to provide a simply constructed, reliable automatic clip or carrier fed gun apparatus for implanting pellets. Further it is an object of the present invention to provide an inexpensive automatic gun apparatus for implanting the pellets. These and other objects will become increasingly apparent by reference to the following description and the drawings.

IN THE DRAWINGS

FIG. 1 is a front cross-sectional view of a pellet implanting gun apparatus 10 wherein a trigger 36 and lever 15 are in their rest positions.

FIG. 2 is a plan partial cross-sectional view along line 2—2 of FIG. 1 wherein a return spring 19 and pusher pin 18 are provided for the lever arm 15.

FIG. 3 is a plan partial cross-sectional view along line 3—3 of FIG. 1 wherein an actuator 16 is shown in engagement with the lever arm 15.

FIG. 4 is a front cross-sectional view of the pellet implanting gun apparatus 10 of FIG. 1 wherein the trigger 36 is depressed and the lever 15 is in a "cocked" position adjacent a cam 101 on carrier 100.

FIG. 5 is a right end cross-sectional view along line 5—5 of FIG. 1 showing the carrier 100 and cam 101 with the lever arm 15 engaging an actuating surface 101b of the cam 101.

Figure 6:
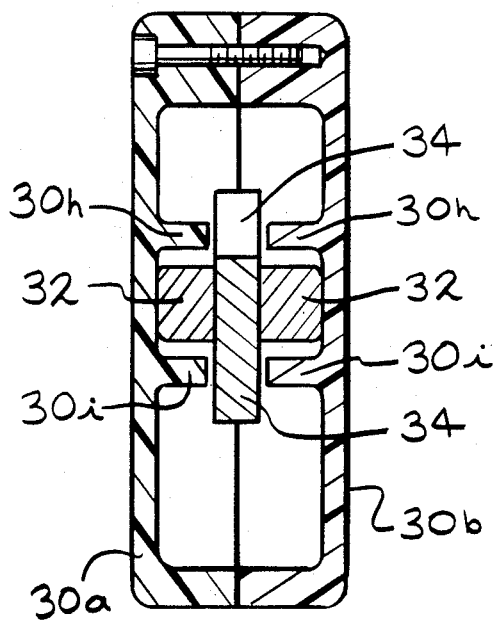

FIG. 6 is a right end cross-sectional view along line 6—6 of FIG. 1 showing a linkage member located in an opening 32a of a rod holder 31.

Figure 7:
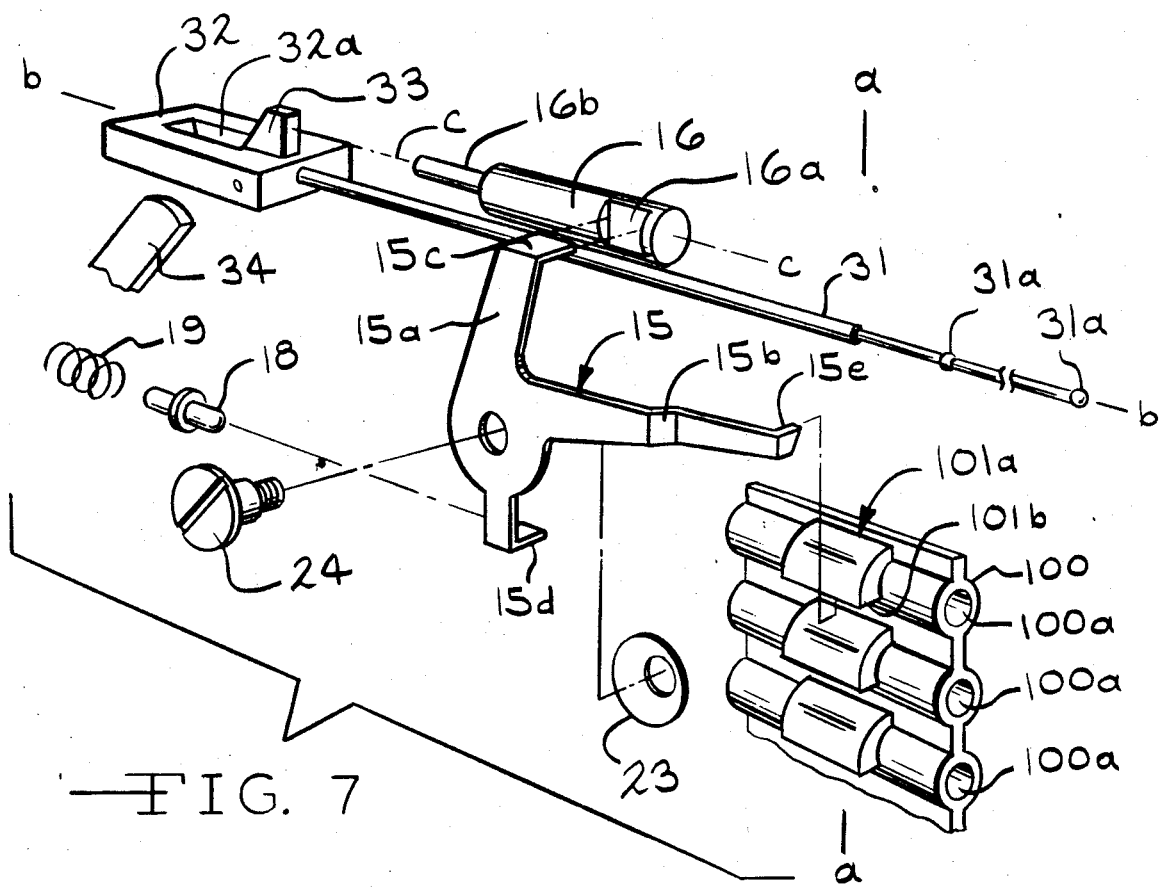

FIG. 7 is a disassembled isometric view showing the relationship of the lever arm 15, rod 31, actuator 16 pusher pin 18 and cams 101a on cam 100.

GENERAL DESCRIPTION

The present invention relates to a hand held gun apparatus for implanting a pellet into an animal which comprises: a hollow needle defining a barrel for implanting the pellet into the animal; a head means on the gun apparatus supporting the needle with an opening through the assembly into the barrel and having a slot for supporting a linearly moveable carrier along a first axis perpendicular to the barrel of the needle, the carrier having multiple spaced apart cam means on one side, and having multiple parallel chambers each adjacent a cam for carrying a pellet; a pistol grip means supporting the head means; a drive rod linearly moveable through an opening between the ends of the head means and into the barrel from the pistol grip; an actuating means mounted in the pistol grip for moving the drive rod into and out of the barrel; trigger means mounted on the pistol grip actuatable by the hand for moving the actuating means and thus drive rod into and out of the barrel; lever means pivotably mounted on the head means actuated by movement of the drive rod into and then from the barrel wherein the lever means is rotated into position over the cam means on the outside of the carrier as a result of the movement of the drive rod into the barrel to implant a first pellet and then the lever means acts on the cam means to move the carrier along the first axis upon release of the trigger means and retraction of the drive rod from the barrel to move a new chamber and pellet into registry between the drive rod and the barrel so that the drive rod can pass through the new chamber and into and through the barrel to implant a second pellet in the animal; and spring means urging the lever means to move the carrier and the new chamber into position between the barrel and drive rod.

In particular the present invention relates to a hand held gun apparatus for implanting a pellet into an animal which comprises: a hollow needle defining a barrel for implanting the pellet into the animal; a head assembly supporting the needle at a first end and having a second end opposite the first end traversed by an opening into the barrel and having a slot for supporting a linearly moveable carrier along a first axis perpendicular to the barrel of the needle, the carrier having multiple spaced apart cams on one side, each cam having an arcuate surface and a drive surface radially of the arcuate surface, the carrier having multiple parallel chambers each adjacent a cam for carrying a pellet; a pistol grip attached to the head assembly at the second end; a drive rod linearly moveable from the pistol grip through the opening between the ends of the head assembly and into the barrel; an actuating means mounted inside of the pistol grip for moving the drive rod into and out of the barrel; trigger means mounted on the pistol grip actuatable by the hand for moving the actuating means and thus the drive rod into and out of the barrel; lever means pivotably mounted in the head assembly actuated by movement of the drive rod into and then from the barrel wherein the lever means is rotated into position over the arcuate surface of the cam on the outside of the carrier as a result of the movement of the drive rod into the barrel to implant a first pellet and then the lever means acts on the drive surface of the cam to move the carrier along the first axis upon release of the trigger means and retraction of the drive rod from the barrel to move a new chamber and pellet into registry between the drive rod and the barrel so that the drive rod can pass through the new chamber and into and through the barrel to implant a second pellet in the animal; and return spring means urging the lever means to move the carrier and the new chamber into position between the barrel and drive rod.

Finally the present invention relates to a carrier device for pellets to be injected by means of a hand held gun apparatus which comprises: an elongate bar having opposed top and bottom ends, opposed front and rear sides and lateral sides between the top and bottom ends and having a plurality of equally spaced apart parallel chambers between top and bottom ends for holding the pellets and adapted to fit in a slot of the gun so that a rod can push a pellet from each chamber into a barrel in a hollow needle for implanting the pellet; and a plurality of spaced apart parallel cams mounted on one lateral side of the bar adjacent each chamber, each cam being identical and defining an arcuate surface and a radial surface to the arcuate surface projecting from the one lateral side wherein the cams are positioned on the one lateral side so as to allow a lever to slide over the arcuate surface and engage the drive surface of the cam to thereby move the carrier in the gun by exerting a force on the radial surface so that the chamber is in registry with the barrel.

Thus the present invention relies upon a pivotable lever to hold and to move the carrier in the automatic gun apparatus. The lever is actuated or "cocked" upon movement of the trigger and the carrier is advanced upon release of the trigger.

SPECIFIC DESCRIPTION

FIGS. 1 to 7 show the gun apparatus 10 of the present invention. In its preferred form it includes a handle assembly 11 and head assembly 12.

The head assembly 12 has a needle 13 with a barrel 13a at one end of a body 14. The body 14 includes a slot 14a (FIG. 6) for movement of a carrier 100 along axis a—a. The head assembly 12 connects to the handle assembly 11 by means of flanges 14b and 14c and bolts 25 between the flanges 14b and 14c through the head assembly 12 in recess 14d. A recess 14e is provided for supporting a lever 15 for pivotable movement. The lever 15 includes a bar 15a and an arm 15b extending from the bar 15a. The ends of the bar 15a have extensions 15c and 15d which extend into slots 14f and 14g of the body 14 (FIGS. 2 and 3). The lever 15 is secured to the body 14 by means of a shoulder screw 24 held in place by wave spring 23 which allows slight movement of the lever 15 outward from the body 14. The arm 15b extends away from the bar 15a and has a projection 15e extending into slot 14h and extending into slot 14a. The body 14 includes holes 14i and 14j leading to slots 14f and 14g.

As shown in FIG. 3, an actuator 16 is provided in hole 14i such that slot 15a engages projection 15c from the lever 14. The actuator 16 is held in place by set screw 17 in body 14. An extension 16b, of the actuator 16 extends away from the body 14. As shown in FIG. 2, a pusher pin 18 is provided in hole 14j which engages projection 15d of lever 15. The pusher pin 18 is biased by a spring 19 which is held in place by set screw 20.

Thus in operation of the head assembly 12, the extension 16b of actuator 16 can be pushed so that slot 16a engages projection 15c and moves the lever 15 clockwise on the shoulder screw 24. The bar 15q compresses spring 19, thus loading the lever 15. As the bar 15a pivots clockwise, the arm 15b also pivots in slot 14h such that projection 15d moves over the arcuate surface 101a of cam 101 on carrier 100 and snaps into place adjacent a radial drive surface 101b. When the pressure on the extension 16b of the actuator 16 is released, the lever arm 15 is pivoted counter-clockwise back to its starting position by spring 19 and extension 15e pushes the radial drive surface 101b of cam 101. Thus moving the carrier 100 upwards along axis a—a to index another opening 100a of carrier 100 between opening 14k leading to barrel 13a. Generally cover plates 21 and 22 cover the slot 14a and opening 14e in use. The handle assembly 11 is used to actuate the lever 15 by means of the extension 16b.

The handle assembly 11 includes a right half 30a and a left half 30b which are mirror images of each other. The halves 30a and 30b have a grip portion 30c and a trigger ring 30d defined by opening 30e. The front of the halves 30a and 30b are provided with two semi-circular grooves 30f and 30g. The upper opening 30f receives the extension 16b. The lower opening 30g receives a drive rod 31 which has an axis in line with the opening 14k and barrel 13a along axis b—b. Rounded portions 31a of rod 31 slide in opening 14k and barrel 13a and reduce friction because of limited surface contact.

The rod 31 is moved between parallel side rails 30 h and 30i on each half 30a and 30b of the handle assembly 11 by a rod holder 32 which slides between the rails 30h and 30i. A pusher 33 extends above the rails 30h to a height corresponding to axis c—c of the actuator 16 and extension 16a. When the rod 31 is moved in rails 30h and 30 i, the pusher 33 engages the extension 16b of the actuator to depress it in the head assembly 12.

A linkage member 34 extends into an opening 32a in the holder 32 and is connected to a trigger 36. The trigger 36 is pivoted on pin 37 mounted on one of the halves 30a and 30b. The linkage member 34 has a slot 34a which slides on a roller bearing 35 on trigger 36. The linkage member is pivoted on pin 38 on trigger 36 which rotates in an arc in slot 36a of the trigger 36. Spring 39 is connected to the bottom of grip 30c and to a mid-point of the linkage member 34 in opening 34b. The halves 30a and 30b are held together by screws 40.

In operation as best seen from FIG. 7, when the trigger 36 is depressed inside the handle assembly 11 the roller bearing slides 35 in slot 34a to pivot the linkage member 34 on pin 38 against the tension of the spring 39. The linkage member 34 thus moves the rod holder 32 and rod 31 out of the handle assembly 11 through the opening 100a in clip or carrier 100, out the barrel 13a on needle 13 to implant a pellet. At the same time, the pusher 33 engages the extension 16a of actuator 16 to move the lever 15 and projection 15e of arm 15b over the arcuate surface 101a of cam 101 so that it snaps into place adjacent radial drive surface 101b. When the trigger 36 is released the carrier is moved by projection 15e engaging the drive surface 101b to move the carrier 100 upwards to align a new opening 100a. Each time the trigger is pulled, a new opening 100a is presented between the rod 31 and the barrel 13a of the needle 13 for injection.

It will be appreciated that the various actuating means can be used to connect the drive rod 31 and the trigger 36. Further, various means can be used for actuating lever 15 as a function of movement of the rod 15. Primarily the need is to rotate and cock the lever 15 so that a drive surface 101b is engaged as the trigger 36 is depressed and then to move the carrier 100 when the trigger 36 is released.

It will be appreciated that various carriers and cam designs can be used, although the clip or carrier 10 and cam 101 design of FIG. 7 is preferred. All that is required is that the rotating lever 15 be able to move the carrier 100.

Numerous variations will occur to those skilled in the art and it is intended that the present invention be limited only to the hereinafter appended claims.

I claim:

1. A hand held gun apparatus for implanting a pellet into an animal which comprises:
    (a) a hollow needle defining a barrel for implanting the pellet into the animal;
    (b) a head means on the gun apparatus supporting the needle with an opening through the assembly into the barrel and having a slot for supporting a linearly moveable carrier along a first axis perpendicular to the barrel of the needle, the carrier having multiple spaced apart cam means on one side, and having multiple parallel chambers each adjacent a cam for carrying a pellet;
    (c) a pistol grip means supporting the head means;
    (d) a drive rod linearly moveable through an opening between the ends of the head means and into the barrel from the pistol grip;
    (e) an actuating means mounted in the pistol grip for moving the drive rod into and out of the barrel;
    (f) trigger means mounted on the pistol grip actuatable by the hand for moving the actuating means and thus drive rod into and out of the barrel;
    (g) lever means pivotably mounted on the head means actuated by movement of the drive rod into and then from the barrel wherein the lever means is rotated into position over the cam means on the outside of the carrier as a result of the movement of the drive rod into the barrel to implant a first pellet and then the lever means acts on the cam means to move the carrier along the first axis upon release of the trigger means and retraction of the drive rod from the barrel to move a new chamber and pellet into registry between the drive rod and the barrel so that the drive rod can pass through the new chamber and into and through the barrel to implant a second pellet in the animal; and
    (h) spring means urging the lever means to move the carrier and the new chamber into position between the barrel and drive rod.

2. The apparatus of claim 1 wherein each of the cam means has an arcuate surface over which the lever means is moved wherein the drive rod is moved into the barrel and has a drive surface radially of the arcuate surface which is engaged by the lever means to move the carrier and to position the new chamber between the drive rod and the barrel.

3. A hand held gun apparatus for implanting a pellet into an animal which comprises:
    (a) a hollow needle defining a barrel for implanting the pellet into the animal;
    (b) a head assembly supporting the needle at a first end and having a second end opposite the first end traversed by an opening into the barrel and having a slot for supporting a linearly moveable carrier along a first axis perpendicular to the barrel of the needle, the carrier having multiple spaced apart cams on one side, each cam having an arcuate surface and a drive surface radially of the arcuate surface, the carrier having multiple parallel chambers each adjacent a cam for carrying a pellet;
    (c) a pistol grip attached to the head assembly at the second end;
    (d) a drive rod linearly moveable from the pistol grip through the opening between the ends of the head assembly and into the barrel;
    (e) an actuating means mounted inside of the pistol grip for moving the drive rod into and out of the barrel;
    (f) trigger means mounted on the pistol grip actuatable by the hand for moving the actuating means and thus the drive rod into and out of the barrel;
    (g) lever means pivotably mounted in the head assembly actuated by movement of the drive rod into and then from the barrel wherein the lever means is rotated into position over the arcuate surface of the cam on the outside of the carrier as a result of the movement of the drive rod into the barrel to implant a first pellet and then the lever means acts on the drive surface of the cam to move the carrier along the first axis upon release of the trigger means and retraction of the drive rod from the barrel to move a new chamber and pellet into registry between the drive rod and the barrel so that the drive rod can pass through the new chamber and into and through the barrel to implant a second pellet in the animal; and
    (h) return spring means urging the lever means to move the carrier and the new chamber into position between the barrel and drive rod.

4. The apparatus of claim 3 wherein the head assembly includes an actuator which moves the lever means over the arcuate surface when a projection from the actuating means or drive rod engages the actuator.

5. The apparatus of claim 4 wherein the return spring means includes a spring loaded pusher pin mounted in the head assembly to engage the lever means.

6. The apparatus of claim 3 wherein the head assembly is attached to the pistol grip by means of screws through spaced apart flanges on the head assembly at the second end.

7. The apparatus of claim 3 wherein the lever means is mounted in a recess in the head assembly, wherein an actuator mounted in the head assembly rotates the lever means over the arcuate surface when a projection from the drive rod or actuating means engages the actuator and wherein the return spring means includes a spring loaded pusher pin mounted in the head assembly which engages the lever means.

8. The apparatus of claim 7 wherein the lever means includes an opening in a bar so that the lever means can be pivotably mounted to the head assembly and wherein the return spring means and actuator engage opposite ends of the bar and includes an arm extending from the bar with an end portion which engages the cam.

9. The apparatus of claim 3 wherein the actuating means includes a pivoted linkage between the trigger means and the drive rod which is spring loaded to extend the trigger means to a rest position after the trigger means is released.

10. The apparatus of claim 9 wherein the linkage is pivoted on the trigger adjacent a slot in the linkage slideably mounted on a roller bearing mounted on the trigger means.

11. The apparatus of claim 3 wherein the linkage is mounted in a slot in a linearly moveable holder for the rod mounted in the pistol grip.

12. A carrier device for pellets to be injected by means of a hand held gun apparatus which comprises:
 (a) an elongate bar having opposed top and bottom ends, opposed front and rear sides and lateral sides between the top and bottom ends and having a plurality of equally spaced apart parallel chambers between top and bottom ends for holding the pellets and adapted to fit in a slot of the gun so that a rod can push a pellet from each chamber into a barrel in a hollow needle for implanting the pellet; and
 (b) a plurality of spaced apart parallel cams mounted on one lateral side of the bar adjacent each chamber, each cam being identical and defining an arcuate surface and a radial surface to the arcuate surface projecting from the one lateral side wherein the cams are positioned on the one lateral side so as to allow a lever to slide over the arcuate surface and engage the drive surface of the cam to thereby move the carrier in the gun by exerting a force on the radial surface so that the chamber is in registry with the barrel.

13. The carrier device of claim 12 wherein the bar has a rectangular cross-section between the sides.

14. The carrier device of claim 12 wherein the carrier has at least five chambers and cams.

* * * * *